(12) United States Patent
Han et al.

(10) Patent No.: US 8,071,514 B2
(45) Date of Patent: *Dec. 6, 2011

(54) SILICONE FUNCTIONALIZED FLUIDS WITH LOW TRACTION CHARACTERISTICS

(75) Inventors: Wenning Wang Han, Lawrenceville, NJ (US); Martin N. Webster, Pennington, NJ (US); Bernie J. Pafford, Berkeley Heights, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 733 days.

This patent is subject to a terminal disclaimer.

(21) Appl. No.: 12/044,604

(22) Filed: Mar. 7, 2008

(65) Prior Publication Data

US 2009/0227481 A1   Sep. 10, 2009

(51) Int. Cl.
*B01D 19/04* (2006.01)
*C10M 169/04* (2006.01)
*C08K 5/00* (2006.01)

(52) U.S. Cl. .............. 508/202; 508/208; 508/212

(58) Field of Classification Search ............... 508/205, 508/202, 208, 212; 556/439, 415, 416
See application file for complete search history.

(56) References Cited

U.S. PATENT DOCUMENTS

| | | | |
|---|---|---|---|
| 3,371,104 A | 2/1968 | Rossmy et al. | |
| 4,378,459 A * | 3/1983 | Hardman et al. | 556/439 |
| 4,725,658 A | 2/1988 | Thayer et al. | |
| 4,956,122 A | 9/1990 | Watts et al. | |
| 5,698,502 A | 12/1997 | Pafford et al. | |
| 5,863,873 A | 1/1999 | Bovington | |
| 6,602,830 B1 * | 8/2003 | Fey et al. | 508/208 |
| 2004/0029407 A1 | 2/2004 | Liu et al. | |
| 2008/0108842 A1 * | 5/2008 | Pafford et al. | 556/439 |

FOREIGN PATENT DOCUMENTS

| | | |
|---|---|---|
| WO | WO 03/091369 | 11/2003 |
| WO | WO 2005/059066 | 6/2005 |
| WO | WO 2005/059066 A1 * | 6/2005 |
| WO | WO 2006/066227 | 6/2006 |

OTHER PUBLICATIONS

Jackson et al., "The Effect of Lubricant Traction on Scuffing," STLE Tribology Transactions, vol. 37 No. 2, Apr. 2, 1994, p. 387-395.
Tuomas et al, "Influence of Molecular Structure on the Lubrication Properties of Four Different Esters," Tribologia, vol. 19 No. 4, 2000, p. 3-8.

* cited by examiner

*Primary Examiner* — Michael Marcheschi
*Assistant Examiner* — Latosha Hines
(74) *Attorney, Agent, or Firm* — Nancy T. Krawczyk

(57) ABSTRACT

A highly branched functionalized silicone backbone lubricating fluid which provides exceptionally low traction, a method of lowering traction coefficients in lubricating compositions, and to uses of such compositions.

22 Claims, 8 Drawing Sheets

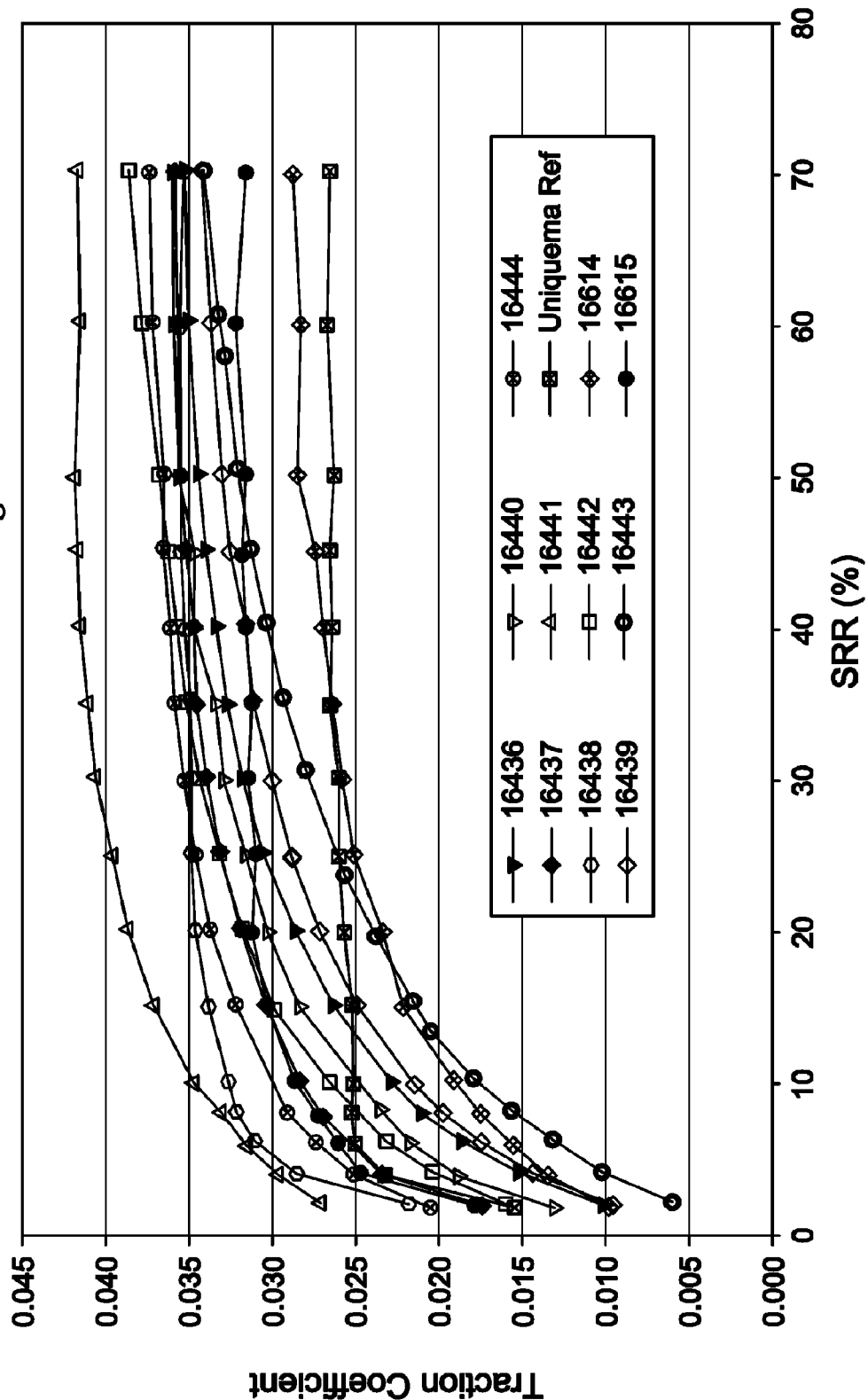

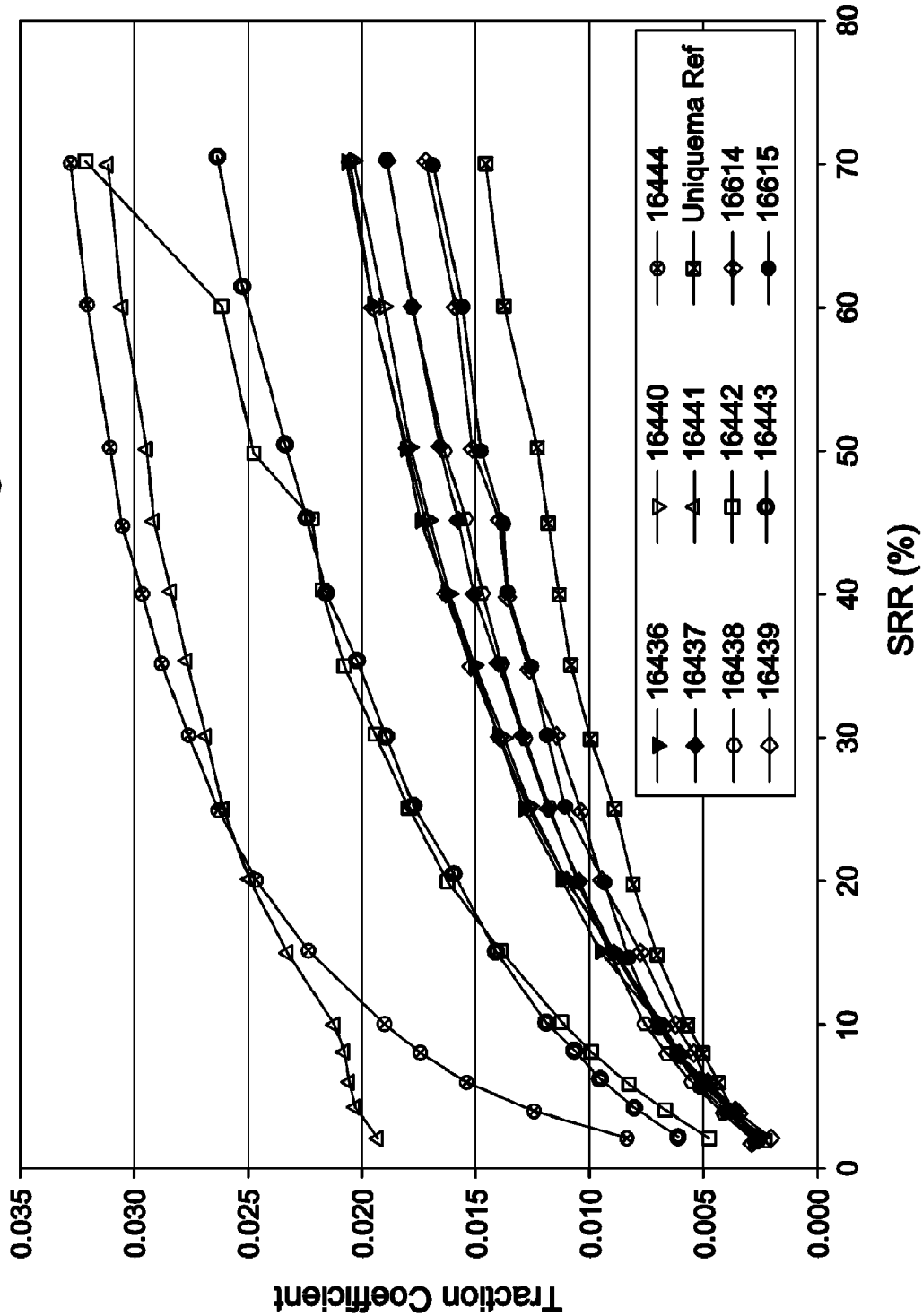

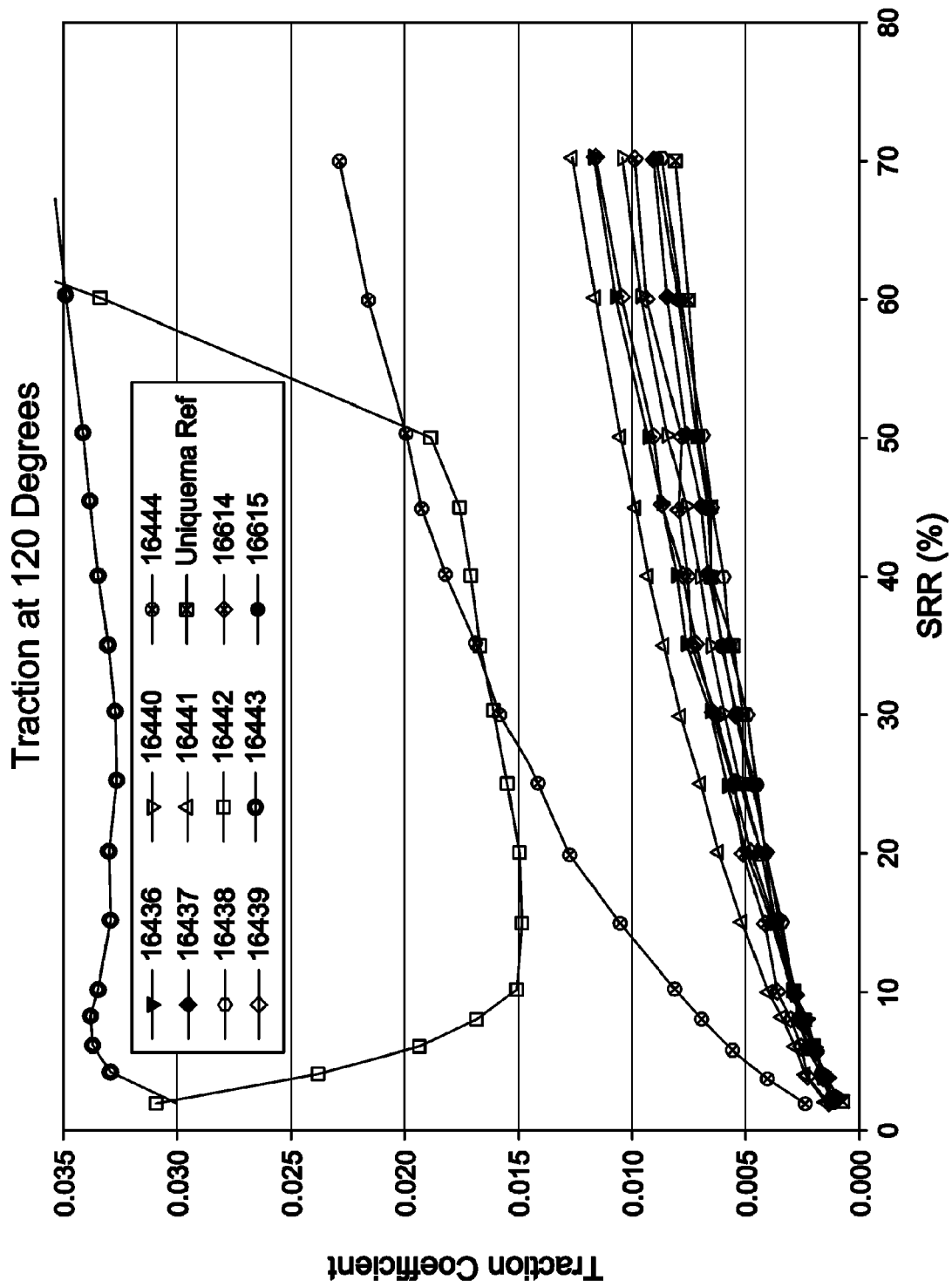

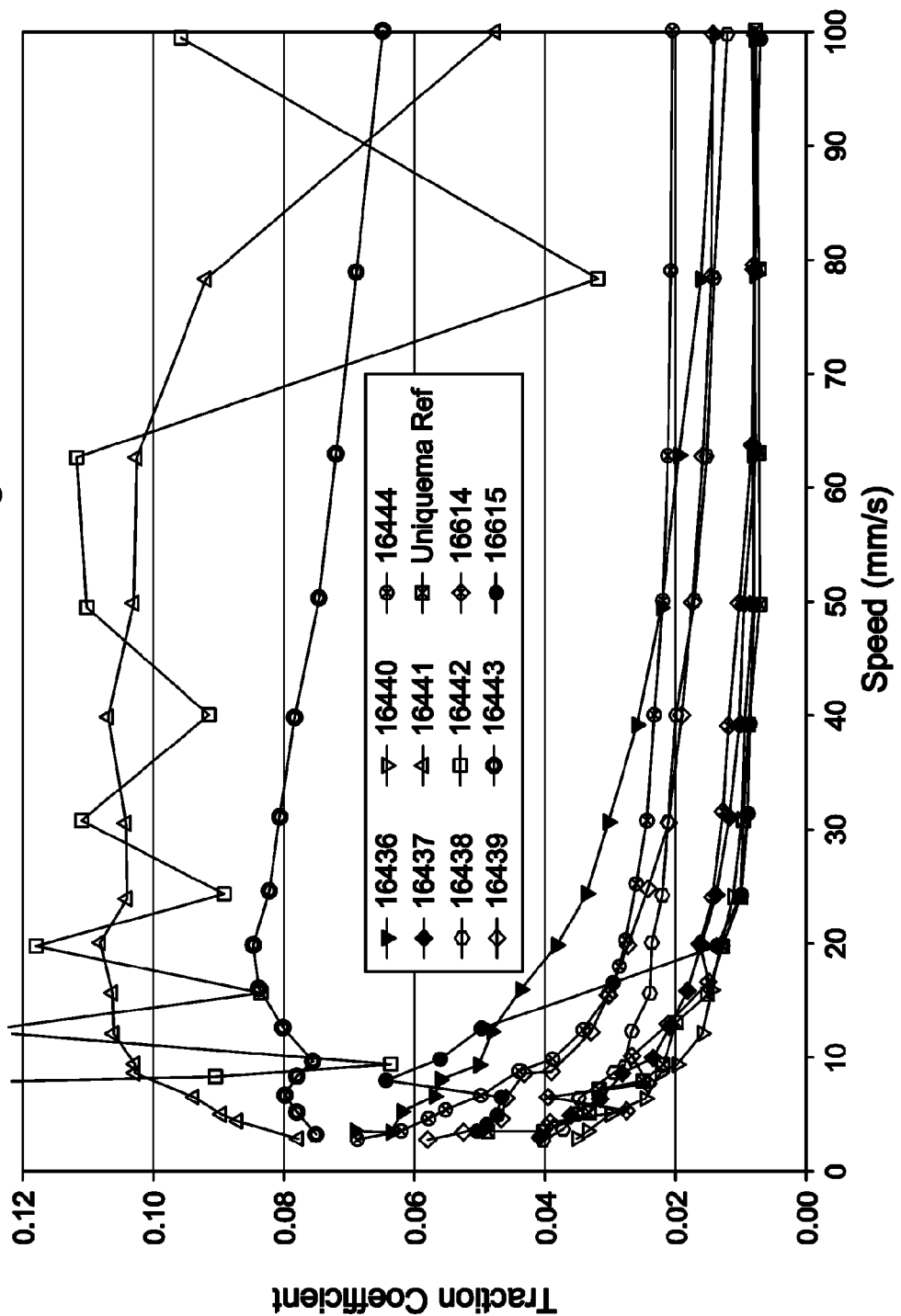

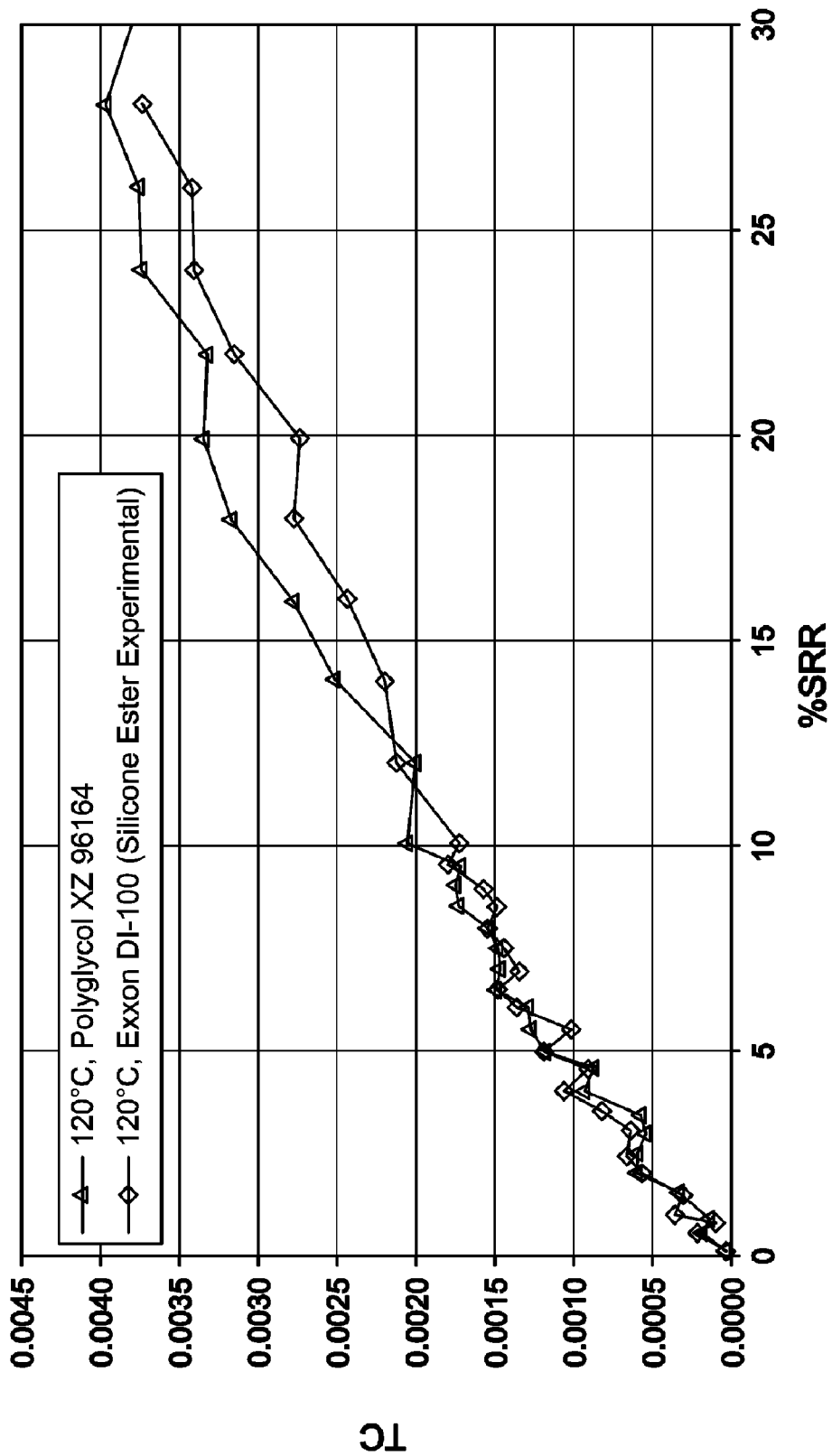

SILICONE FUNCTIONALIZED FLUIDS WITH LOW TRACTION CHARACTERISTICS

FIELD OF THE INVENTION

This disclosure relates to silicone functionalized fluids. Specifically, it is directed to compositions that provide exceptionally low traction, a method of lowering traction coefficients in lubricating compositions, and the uses of such compositions. In particular, the silicone functionalized lubricating fluids of the present disclosure include silicone based fluids having silicon groups and organic groups linked through ester linkages. More particularly, the present disclosure relates to silicone based fluids that are formed from the reaction of vinyl-terminated carboxylic acid esters of partially esterified esters with hydride containing polysiloxanes. The vinyl-terminated carboxylic acid esters of partially esterified esters are formed from the reaction of multifunctional alcohols with vinyl-terminated carboxylic acids.

BACKGROUND OF THE INVENTION

Elastohydrodynamic lubrication (EHL) is the mode of lubrication that exists in non-conforming concentrated contacts. Examples include the contact between meshing gear teeth used in hypoid axles, worm gears, etc. and between the components in a rolling element bearing. In these contacts the load is supported over a very small contact area which results in very high contact pressures. As lubricants are drawn into the contact zone by the movement of the component surfaces, the lubricant experiences an increase in pressure. Pressures on the order of 1 GPa and above are common in EHL contacts. Most lubricating oils exhibit a large increase in viscosity in response to higher pressures. It is this characteristic that results in the separation of the two surfaces in the contact zone.

If there is relative sliding between the two contacting surfaces in the central contact region, the lubricant is sheared under these high-pressure conditions. The shearing losses depend on how the oil behaves under these extreme conditions. The properties of the oil under high pressure, in turn, depend on the type of base stocks used in the manufacture of the finished lubricant. The generation of the EHL film is governed by what happens in the inlet region of the contact; however, the energy losses are governed by what happens when the lubricant is sheared in the high-pressure central contact region.

The resistance of the lubricant to the shearing effects within an EHL contact is referred to as traction. This is not to be confused with friction, which is associated with surface interactions. The traction response is dominated by the shear behavior of the lubricant in the central high contact pressure region of an EHL contact. The traction properties generally depend on the base stock type.

Traction coefficients can be defined as the traction force divided by the normal force. The traction force is the force transmitted across a sheared EHL film. The normal force or contact load is the force of one element (such as a roller) pushing down on a second element. Therefore, the traction coefficient is a non-dimensional measure of the shear resistance imparted by a lubricant under EHL conditions. Lower traction coefficients result in lower shearing forces and hence less energy loss if the two surfaces are in relative motion. Low traction is believed to be related to improved fuel economy, increased energy efficiency, reduced operating temperatures, and improved durability.

PAO has a much lower traction coefficient, relative to mineral oil, over the range of slide-roll ratios, pressures and temperatures evaluated. This means that less energy will be required to shear the EHL film which separates moving surfaces. When gear oils are formulated based on PAO vs. mineral oil, one sees the same lowering of the traction coefficient. This concept is well documented in the industry.

It is also well documented that certain types of synthetic base stocks, such as polyalkylene glycols (PAG), can provide reduced traction over a wide range of conditions. U.S. Pat. No. 4,956,122 discloses combinations of high and low viscosity synthetic hydrocarbons. A composition is claimed comprising a PAO having a viscosity of between 40 and 1000 cSt (100° C.), optionally further comprising a synthetic hydrocarbon having a viscosity of between 1 and 10 cSt (100° C.), a carboxylic acid ester having a viscosity of between 1 and 10 cSt (100° C.), an additive package, and mixtures thereof.

U.S. Pat. No. 5,863,873 teaches a composition comprising a base oil having a viscosity of about 2.5 to about 9 cSt (or $mm^2/s$) at 100° C. as a major component and a fuel economy improving additive comprising a polar compound with a viscosity greater than the bulk lubricant present from 2 to about 15 wt % of the composition. The compositions are said to improve fuel economy in an internal combustion engine.

Publication WO03/091369 discloses lubricating compositions comprising a high viscosity fluid blended with a lower viscosity fluid, wherein the final blend has a viscosity index greater than or equal to 175. In an embodiment, the high viscosity fluid is preferably a polyalphaolefin and/or the lower viscosity fluid comprises a synthetic hydrocarbon. In another embodiment, the novel lubricating compositions of the present invention further comprise one or more of an ester, mineral oil and/or hydroprocessed mineral oil.

Publication US2004/029407 discloses lubricating compositions comprising high viscosity PAOs blended with a lower viscosity ester, wherein the final blend has a viscosity index 5 greater than or equal to 200, including a composition comprising a PAO having a viscosity of greater than or equal to about 40 cSt at 100° C. and less than or equal to about 1,000 cSt at 100° C.; and an ester having a viscosity of less than or equal to about 2.0 cSt at 100° C., wherein said blend has a viscosity index greater than or equal to about 200.

"Effect of Lubricant Traction on Scuffing", STLE Tribology Transactions, Vol. 37 No., Apr. 2, 1994, p. 387-395 reported the use of low traction PAO-based lubricants with mineral oils in basestock, antiwear and extreme pressure (EP) formulations and at both high (greater than 6) and moderate (approximately 1.2) specific film thickness lambda. At lambda greater than 6, the benefits of the synthetics over their mineral counterparts ranged from 25 percent to 220 percent and at lambda nearly 1.2, the benefits were a uniform 40 percent. It was particularly interesting to observe that the antiwear PAO-based oil gave a similar scuff load per unit contact width to an EP mineral gear oil. In addition, it was shown that scuffing load increased with decreasing traction coefficient.

"Influence of Molecular Structure on the Lubrication Properties of Four Different Esters", Tribologia, Vol. 19 No. 4, 2000, p. 3-8, compared the lubricating properties of esters. The lubrication properties that were expected to be dependent on chemical structure such as film thickness and traction, viscosity and friction coefficients were compared by experiment. The results showed that molecular length has a significant influence on lubrication properties, with longer molecules giving the highest viscosity and greatest film thickness. The length of the molecule did not influence the coefficients of friction, but the traction coefficient, gamma, decreased with increasing molecular length.

In lubricant applications, low traction is aimed in order to reduce energy losses. Water soluble polyalkylglycols are currently the best traction fluids available. However, they are not compatible with hydrocarbon based fluids, such as polyalphaolefins (PAO). Stringy solid often appears when mixing the two and creates devastating plugging problems in equipment. Reducing friction under thin film conditions will also reduce energy losses in mechanical systems. Reduced friction can be obtained using friction modifier additive components. However, some synthetic lubricant base stocks may also yield significant benefits over more conventional refined base stocks. Reduced friction performance from the base stock make it possible to avoid the use of a friction modifier enabling reduction in additive metals and ash content and some of the other performance detriments associated with friction modifier components.

Silicone compounds also have a number of positive attributes, including excellent thermal stability. However, limited solubility in a variety of hydrocarbons reduces their potential lubricant applications.

The present inventors have unexpectedly discovered that highly branched functionalized silicone backbone products have different solubility characteristics, thermal stability, and other properties that go beyond conventional lubricants. The highly branched functionalized silicone backbone products of the present disclosure improves compatibility with polyalkylglycols, hydrocarbons, and traditional silicone fluids, thereby making it easy to bridge formulations. The high viscosity index and low traction coefficient of highly branched functionalized silicone backbone products make them comparable in performance to polyalkylglycols. These unique highly branched functionalized silicone backbone products of the present disclosure also exhibit very good oxidation performance.

In addition the highly branched functionalized silicone backbone products of the present disclosure are compatible with other conventional basestocks, such as PAO's, mineral oils, etc., whereas PAG's will form undesirable string solid material and require cleaning of engine before use. However, since highly branched functionalized silicone backbone products of the present disclosure are compatible with such other basestocks, it can be readily mixed therewith out the need to clean out an engine before use. Furthermore, the highly branched functionalized silicone backbone products of the present disclosure exhibit enhanced traction coefficient versus PAG at certain temperatures and pressures, e.g. 0.75 GPa/ 120° C.

SUMMARY OF THE INVENTION

The disclosure is directed to highly branched functionalized silicone backbone lubricant composition having low traction characteristics, and desirable solubility and thermal stability properties.

In some embodiments, the highly branched functionalized silicone backbone products of the present disclosure, may be used as basestock alone, or blended with at least one other Group I-V basestocks, optionally with additives and/or viscosity index (VI) improvers.

A low traction lubricating composition having a traction coefficient of less than or equal to 0.02 as measured using a Mini Traction Machine, the composition comprising a highly branched functionalized silicone backbone. Preferably, the Mini Traction Machine is operated under the following conditions: 2 m/s entraining velocity, a percent slide to roll ratio of 10, 0.75 inch steel ball loaded against a steel disc, and 6.58N applied load and a bulk lubricant temperature of 100° C.

In another embodiment, the highly branched functionalized silicone backbone lubricant can be used as a traction reducer, blended with other fluids, wherein the resulting blend has a traction coefficient lower than the traction coefficient of the fluid by itself.

It is another object of the disclosure to provide useful compositions exhibiting low traction coefficients.

It is still another object of the disclosure to provide low traction coefficient lubricants suitable for use in machine elements in which sliding and rolling is observed, i.e., non-conforming concentrated contacts, such as with roller and spherical bearings, hypoid gears, worm gears, and the like. Such highly branched functionalized silicone backbone lubricant compositions exhibit low traction properties which will reduce the losses in components that contain sliding EHL contacts.

These and other embodiments, objects, features, and advantages will become apparent as reference is made to the following detailed description, including figures, tables, preferred embodiments, examples, and the appended claims.

BRIEF DESCRIPTION OF THE DRAWINGS

FIG. 1(a) is a chart plotting traction coefficient versus SRR % at 40° for various lubricants.

FIG. 2(a) is a chart plotting traction coefficient versus SRR % at 80° for various lubricants.

FIG. 3(a) is a chart plotting traction coefficient versus SRR % at 120° for various lubricants.

FIG. 3(b) is a chart plotting traction coefficient versus Speed (mm/s) at 120° for various lubricants.

FIG. 4(b) is a chart plotting traction coefficient versus SRR % for Dow Polyglycol XZ and Exxon DI-100.

DETAILED DESCRIPTION OF THE PREFERRED EMBODIMENT

Figure 1B:
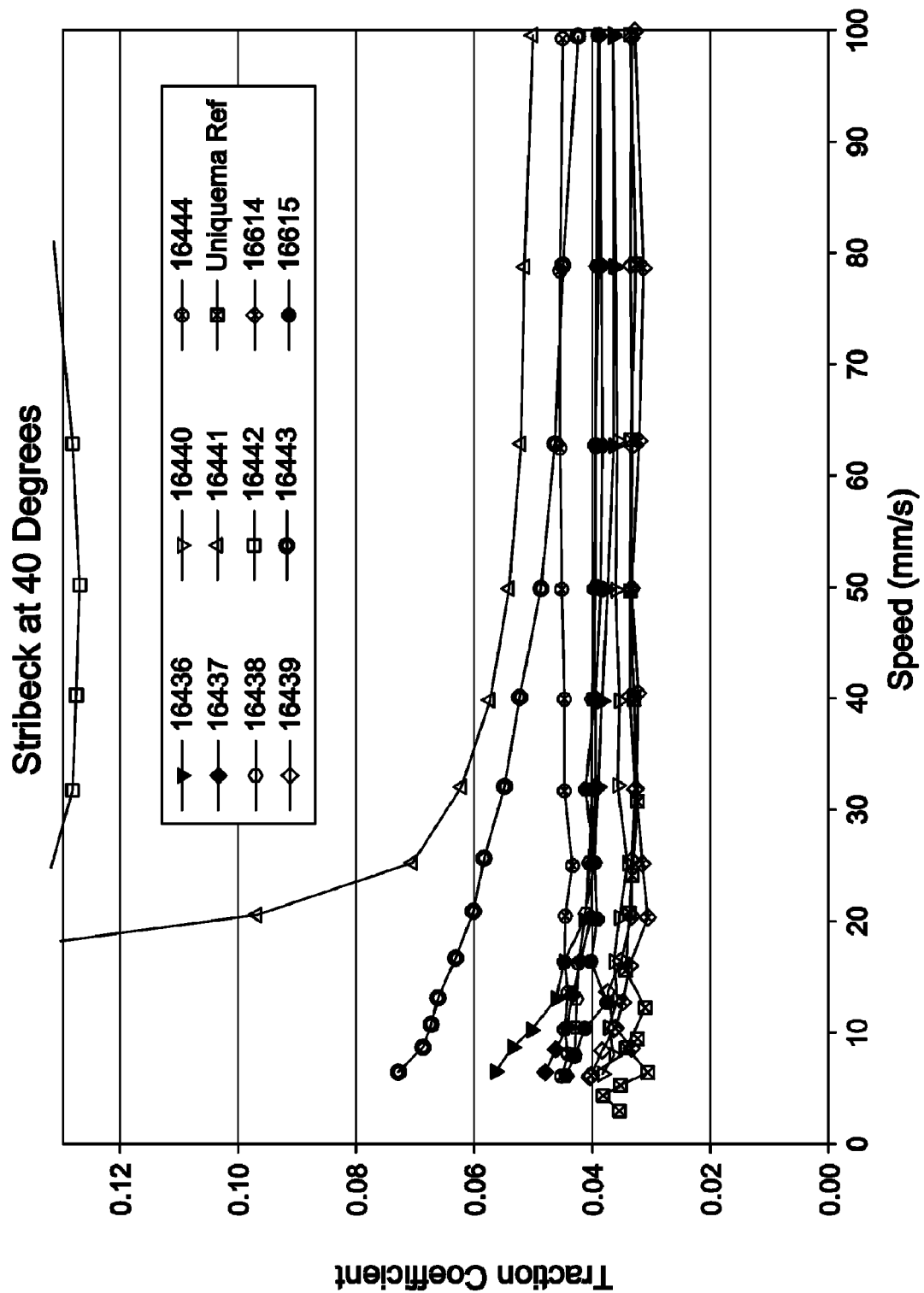
FIG. 1(b) is a chart plotting traction coefficient versus Speed (mm/s) at 40° for various lubricants.

The disclosure is directed to low traction coefficient lubricants and lubricant compositions in the preparation of finished gear, transmission, engine, and industrial lubricants and in a preferred embodiment are used as lubricants for non-conforming concentrated contacts with high sliding such as spur gears, helical gears, hypoid gears, bevel gears, worm gears and the like.

In an embodiment, the low traction coefficient highly branched functionalized silicone backbone lubricants are used alone as low traction fluid, or are, optionally, blended with traction reducers, or be the traction reducers, which may be used to modify the silicone basestock to produce compositions having lower traction coefficients than the basestock by itself or the highly branched functionalized silicone backbone lubricant can be used by itself.

The silicone basestock of the present disclosure is preferably highly branched functionalized silicone backbone is preferably a silicone composition having the formula:

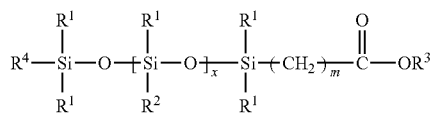

wherein:

$R^1$ are independently selected from the group consisting of: an alkyl having 1-5 carbon atoms, a substituted alkyl having 1-5 carbon atoms optionally substituted by one or more fluorine atoms, and a phenyl, and $R^2$ is selected from the group consisting of: hydrogen, alkyl of 1 to 45 carbon atoms, substituted alkyl of 1 to 45 carbon atoms optionally substituted by one or more fluorine atoms, aryl, an ester-containing group represented by the formula:

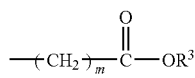

and a reverse ester thereof represented by the formula:

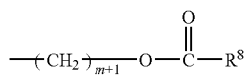

and the formula:

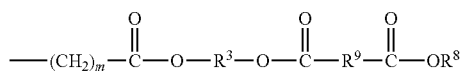

and a reverse ester thereof represented by the formula:

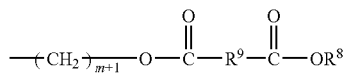

provided that if $R^1$ is anything but methyl or ethyl, then $R^2$ must be a methyl, ethyl or butyl, $R^3$ is derived from a partially esterified ester residue, e.g., for a partially esterified trimetholpropane shown here, the residue is the structure without the remaining free hydroxyl group

| Partial Ester | Residue |
|---|---|
| CH2OOC(CH2)5CH3 <br> \| <br> H5C2—C—CH2OH <br> \| <br> CH2OOC(CH2)5CH3 | CH2OOC(CH2)5CH3 <br> \| <br> H5C2—C—CH2— <br> \| <br> CH2OOC(CH2)5CH3 |

Where in this case the two esterified groups on the molecule have been reacted with heptanoic acid.

$R^8$ is selected from the group consisting of: hydrogen, alkyl of 1 to 45 carbon atoms, substituted alkyl of 1 to 45 carbon atoms optionally substituted by one or more fluorine atoms, aryl and a compound derived from a partially esterified ester residue;

$R^9$ is selected from the group consisting of: an arylene, an alkylene of 1 to 22 carbon atoms, substituted alkylene of 1 to 22 carbon atoms optionally substituted by one or more fluorine atoms and arylene;

$R^4$ is selected from the group consisting of: alkyl of 1 to 45 carbon atoms, substituted alkyl of 1 to 45 carbon atoms optionally substituted by one or more fluorine atoms, aryl, said ester-containing group and said compound derived from reverse esters thereof;

m is an integer between about 5 to about 22; and x is an integer between about 0 to about 1000; wherein said composition has at least 1 compound derived from said partially esterified ester-containing group or and said reverse ester thereof.

Preferably, $R^1$ and $R^2$ are both methyl groups and m is an integer between about 10 to about 14, preferably m is 10. Moreover, x is an integer in the range between about 6 to about 110, preferably between about 6 to about 50.

The compound derived from said partially esterified ester residue is a partially esterified alcohol. The mono-hydroxy-terminated partially esterified alcohol is derived from a polyfunctional alcohol represented by the formula:

$$R^5(OH)_n$$

wherein:

$R^5$ is an n-functional hydrocarbon; and n is from about 2 to about 8, preferably between about 2 to about 4.

The functional alcohol is preferably selected from the group consisting of: ethylene glycol, propylene glycol, butylene glycol, polyethylene glycol, neopentyl glycol, polypropylene glycol, glycerin, trimethylolethane, trimethylolpropane, pentaerythritol, di-pentaerythritol, tri-pentaerythritol, and a mixture thereof. The preferred functional alcohol is trimethylolpropane.

The compound derived from the partially esterified ester residue is a partially esterified acid. The mono-hydroxy-terminated partially esterified acid is derived from multi-functional acids. The functional acid can be selected from the group consisting of any C2 to C 12 diacids, e.g., adipic, azelaic, sebacic, and dodecanedioc, succinic acid, glutaric acid, maleic acid, phthalic acid, trimellitic acid, nadic acid, methyl nadic acid, hexahydrophthalic acid and mixtures thereof.

Anhydrides of polybasic acids can be used in place of the multifunctional acids. The functional anhydride is selected from the group consisting of: succinic anhydride, glutaric anhydride, adipic anhydride, maleic anhydride, phthalic anhydride, trimellitic anhydride, nadic anhydride, methyl nadic anhydride, hexahydrophthalic anhydride, and mixtures thereof.

$R^4$ is preferably a group represented by the formula:

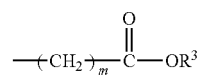

wherein:

$R^3$ is a compound derived from a partially esterified ester residue;

m is an integer in the range between about 5 to about 22; and x is an integer in the range between about 0 to about 1000, or a reverse ester thereof represented by the formula:

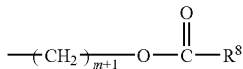

wherein $R^8$ is selected from the group consisting of: hydrogen, alkyl of 1 to 45 carbon atoms, substituted alkyl of 1 to 45 carbon atoms optionally substituted by one or more fluorine atoms, aryl and a compound derived from a partially esterified ester residue.

Alternatively, $R^4$ is a methyl group.

The silicone composition represented by the formula:

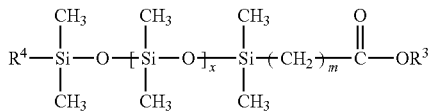

wherein:

$R^4$ is selected from the group consisting of methyl and a group represented by the formula:

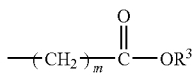

$R^3$ is a compound derived from a partial ester residue;

m is 10; and x is an integer in the range between about 0 to about 1000, preferably about 6 to about 110.

$R^4$ is preferably a group represented by the formula:

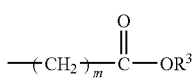

wherein $R^3$ is a compound derived from a partially esterified ester residue.

The partially esterified ester residue is derived from a mono-hydroxy-terminated partially esterified alcohol. The mono-hydroxy-terminated partially esterified alcohol is derived from di-, tri- or tetra-functional alcohol represented by the formula:

wherein:

$R^5$ is an n-functional hydrocarbon residue; and n is an integer in the range between about 2 to about 8, preferably between about 2 to about 4.

Preferably, the di-, tri- or tetra-functional alcohol is selected from the group consisting of: ethylene glycol, propylene glycol, butylene glycol, polyethylene glycol, neopentyl glycol, polypropylene glycol, glycerin, trimethylolethane, trimethylolpropane, pentaerythritol, di-pentaerythritol, tri-pentaerythritol, and a mixture thereof.

Preferably, the functional alcohol is trimethylolpropane and $R^4$ is a group represented by the formula:

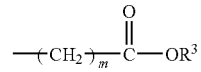

wherein:

$R^3$ is a compound derived from a partially esterified ester residue;

m is an integer in the range between about 5 to about 22; and x is an integer in the range between about 0 to about 1000, or a reverse ester thereof represented by the formula:

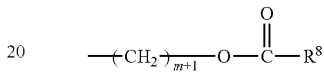

wherein $R^8$ is selected from the group consisting of: hydrogen, alkyl of 1 to 45 carbon atoms, substituted alkyl of 1 to 45 carbon atoms optionally substituted by one or more fluorine atoms, aryl and a compound derived from a partially esterified ester residue. Alternatively, $R^4$ is a methyl group.

The partially esterified ester is represented by the formula:

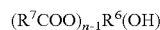

wherein:

$R^6$ is an (n−1)-functional hydrocarbon residue group;

$R^7$ is a hydrocarbyl group; and n is an integer in the range between about 2 to about 8.

According to another embodiment of the present disclosure, a silicone composition is represented by the formula:

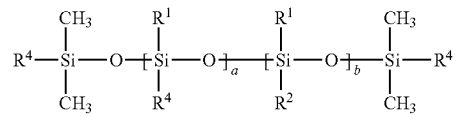

wherein $R^4$ is selected from the group consisting of: alkyl and a group represented by the formula:

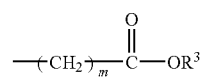

wherein:

a is an integer in the range between about 1 to about 20;

b is an integer in the range between about 0 to about 1000;

$R^3$ is a compound derived from a partially esterified ester residue; and m is an integer in the range between about 5 to about 22;

with the proviso that the $R^4$ groups are not all alkyls.

In the case of blends, it is critical that the traction reducer be miscible with the highly branched functionalized silicone backbone lubricant composition and other traction reducer compositions be miscible with one another. Otherwise the reduction in the traction coefficient of the resulting lubricating composition would be severely reduced. The term miscible takes its ordinary meaning of "the ability to mix in all proportions". The inventors further define the meaning of this term as used herein to specify that miscibility is determined at 25° C. and 1 atm.

The aforementioned blends may be combined with additive packages, thickeners, defoamants, VI improvers, pour point depressants, extreme pressure agents, anti-wear additives, demulsifiers, haze inhibitors, chromophores, anti-oxidants, dispersants, detergents, anti-rust additives, metal passivators, and the like, to provide lubricating oils for various automotive and industrial applications.

Compositions according to the present invention are particularly useful in applications wherein there are EHL contacts that have a component of sliding. Examples include spherical roller bearings, deep groove ball bearings, angular contact bearings among others. Additionally, most gear systems contain multiple sliding EHL contacts between meshing gear teeth. Examples include spur gears, helical gears, hypoid gears, bevel bears, worm gears, and the like.

Rolling element bearings have many configurations and depending on the type of configuration, there may or may not be a benefit to having a lower traction fluid. Where there is sliding between the ball and the raceway, the oil is being sheared such that the reduced traction properties of the highly branched functionalized silicone backbone lubricant compositions described in this disclosure will reduce the energy losses.

The present disclosure is particularly beneficial in any system that includes machine elements that contain gears of any kind and rolling element bearings. Examples of such systems include electricity generating systems, industrial manufacturing equipment such as paper, steel and cement mills, hydraulic systems, automotive drive trains, aircraft propulsion systems, etc. It will be recognized by one of ordinary skill in the art in possession of the present disclosure that the various embodiments set forth herein, including preferred and more preferred embodiments, may be combined in a manner consistent with achieving the objectives of the present disclosure. Thus, by way of example, a preferred embodiment of the present disclosure includes a lubricating composition comprising:

(a) at least one highly branched functionalized silicone backbone lubricant basestock having a viscosity greater than 2 cSt at 100° C. (ASTM D-445);

(b) optionally, at least one other fluid, the fluid characterized by being miscible with basestock (a), wherein (a) is present in the amount of from 1 to 99 wt. %, and (b) is present in the amount of 99 wt. % to 1 wt. %, based on the weight of said lubricating composition; and wherein the lubricating composition is characterized by a traction coefficient less than the traction coefficient of (a) or (b), or the said formulation where one of the fluids (a) was not (a) for every percent slide-to-roll ratio greater than or equal to 5% (or greater than 5% or from greater than 5% to 30% or from 5% to 20%, or greater than or equal to 20%, or greater than 20%), measured over the operating range of 0.1 to 3.5 GPa peak contact pressure, −40° C. to 200° C. lubricant temperature, with a lubricant entraining velocity of from 0.25 to 10.0 m/s; wherein said the resultant lubricant composition is characterized by having a traction coefficient at least 5% lower, preferably 10% lower, more preferably 20% lower, still more preferably 30% lower, yet still more preferably 40% lower, yet again more preferably 50% lower than the traction coefficient of (a) or (b), or the said formulation where one of the fluids (a) was not (a) for every percent slide-roll ratio from 5 to 30; wherein the composition(s) may further comprising thickeners, VI improvers, pour point depressants, extreme pressure agents, anti-wear additives, friction modifiers, demulsifiers, haze inhibitors, chromophores, anti-oxidants, dispersants, detergents, defoamants, anti-rust additives, metal passivators, limited slip additives, and mixtures thereof, wherein said lubricating composition is further characterized as formulated so as to be suitable for use as an automatic transmission fluid, a manual transmission fluid, an axle lubricant, a transaxle lubricant, an industrial gear lubricant, a circulating lubricant, an open gear lubricant, an enclosed gear lubricant, an hydraulic/tractor fluid, or a grease; wherein said lubricating composition is further characterized as formulated so as to be suitable for use as an automotive gear lubricating composition; wherein said lubricating composition is further characterized by a traction coefficient of less than 0.15, preferably from 0.15 and 0.0001, more preferably 0.015 to 0.001, measured over the operating range for determination of traction performance of 0.1 GPa to 3.5 GPa peak contact pressure, at −40° C. to 200° C. lubricant temperature and at % slide-to-roll ratios of greater than 20%, with a lubricant entraining velocity 0.25 m/s to 10 m/s; and also to a method of reducing the traction coefficient of a lubricant composition comprising the highly branched functionalized silicone backbone lubricant basestock having a viscosity greater than 2 cSt at 100° C. (ASTM D-445), the method comprising adding a traction reducer to the lubricant composition in an amount sufficient to reduce the traction coefficient of the lubricant composition for every percent slide-roll ratio greater than or equal to 5, measured over the operating range of 0.1 to 3.5 GPa peak contact pressure, at −40° C. to 200° C. lubricant temperature, with a lubricant entraining velocity of from 0.25 to 10.0 m/s The highly branched functionalized silicone backbone of the present disclosure leads to a hybrid product with different solubility characteristics, thermal stability, and other properties that go beyond current materials. The improved compatibility with polyalkylglycols, hydrocarbons, and traditional silicone fluids makes it easy to bridge formulations. Its high viscosity index and low traction can be comparable to polyalkylglycol. In some instances, the highly branched functionalized silicone backbone of the present disclosure exhibited lower friction properties compared with PAO. The silicone backbone also exhibited very good oxidation performance.

Partially reacted polyol esters provide the desired branching and reactive intermediate. The partial esters can react with an olefinic acid or alcohol and then hydrosilated, or react with a silicone-olefinic acid or silicone-olefinic alcohol. The final product may contain part or none of the fully esterified esters from the initial ester reactant.

It has been unexpectedly discovered by the present inventors that the highly branched functionalized silicone backbone of the present disclosure exhibits better traction performance than conventional hydrocarbons, PAO and esters. This silicone backbone product has comparable traction performance to water soluble polyalkylglycol (PAG) of similar viscosity. See Table 1 below:

TABLE 1

| Lubricant Product** | KV 100° C./VI | Wt % Free Ester* |
|---|---|---|
| 16436 Exxon Di-10 | 11.24/211 | 56 |
| 16437 Exxon Di-45 | 20.22/304 | 32 |
| 16438 Exxon Di-100 | 71.41/360 | 25 |
| 16439 Exxon D2 | 20.04/204 | 61 |
| 16440 Exxon D10 | 36.68/280 | 49 |
| 16441 Siltech Di-45 | 17.07/436 | 0 |
| 16442 Siltech D2 | 3.81/515 | 0 |
| 16443 C8/C10 TMP Ester | 4.30/136 | 100 |
| 16444 SpectraSyn 40 | 42.00/145 | 0 |

TABLE 1-continued

| | | |
|---|---|---|
| Uniqema Emkarox VG 330W | 56.00/239 | 0 |
| 16614 Exxon Di-45P MR 18-80 | 70.63/341 | ~2 |
| 16615 Exxon Di-100P MR 18-82A | 121.70/397 | ~2 |
| 16852 Exxon D10P Mr18-85P | n/a | ~2 |

*Fully esterified non-silicone containing fluid can be produced during the process. It is referred to as free ester,
e.g., free ester in Table 1

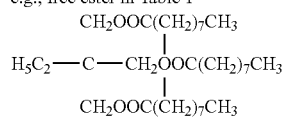

**Lubricant Product Structure—Exxon Di-10 where x = 10, Exxon Di-45 where x = 45, Exxon Di-100, where x = 100 (reference silicone basestock structure on pg 8)
$R^1 = R^2 = -CH_3$, $R^4 = -(CH_2)_m-C(=O)-O-R^3$ where m = 10
wherein $R^3$ is

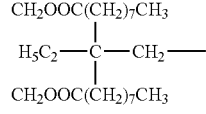

Exxon D2 where a=b=4, Exxon D10 where a=36 b=4 (reference silicone basestock structure on pg 14)

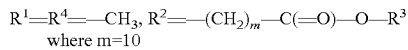

wherein $R^3$ is

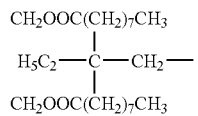

FIGS. 1a-4b show data obtained using a PCS Instruments Mini Traction Machine (MTM).

Mini Traction Machine

The MTM2 is the latest evolution of the successful MTM instrument which to date has sold over 50 systems worldwide. It is a flexible general purpose instrument for measuring the frictional properties of lubricated and unlubricated contacts under a wide range of rolling and sliding conditions. One of the main applications is the fully automated traction mapping of lubricants under conditions commonly found in internal combustion engines.

Additional features allow the measurement of anti-wear additive film growth on test specimens, investigation of soft contacts, reciprocating friction and wear measurements.

MTM Principle

In the standard configuration the test specimens are a 19.05 mm (¾ inch) steel ball and a 46 mm diameter steel disc. The ball is loaded against the face of the disc and the ball and disc are driven independently to create a mixed rolling/sliding contact. The frictional force between the ball and disc is measured by a force transducer. Additional sensors measure the applied load, the lubricant temperature and (optionally) the electrical contact resistance between the specimens and the relative wear between them.

Automated Testing

The control software runs on a standard PC and allows the user to easily define a test profile containing a sequence of temperatures, loads and speeds.

The selected profile steps the instrument through the test sequence, recording data as required, without any intervention by the user. The design parameters of the instrument have been carefully chosen so that high contact pressures, temperatures and speeds can be attained within a safe, easy to use laboratory bench 3D Spacer Layer Imaging Method (SLIM)

3D Spacer Layer Imaging Method (SLIM) enables the instrument to measure additive film formation on the test ball during the course of a test. This option is of great benefit to users who are designing and developing lubricants and additive packages.

Electrical Contact Resistance (ECR)

Electrical Contact Resistance (ECR) gives an indication of film thickness between the two specimens.

Reciprocating Option

Reciprocating option enables the disc to be driven with a sinusoidal motion, further expanding the range of contact conditions which can be created.

MTM2 Accessories

PCS has developed a wide range of accessories for the MTM2. Some of them were developed to extend the capabilities of the instrument, such as the grease scoop which maintains grease within the contact during a test. Others were designed to meet the specialised needs of some customers, such as the mini pot and pot filler which greatly reduce the volume of sample fluid required.

Specimens Selection

The standard ball and disc specimens can be made from almost any combination of materials, including metals, ceramics, polymers, elastomers and coated substrates. The simple specimen geometry and small size means that the specimens are usually sufficiently inexpensive that they can be treated as single-use.

Material

The standard disc and ball are made of 52100 steel (760 HV). Other materials are available including AISI8620 steel, tungsten carbide, aluminium, copper and brass. Contact PCS to discuss alternative material. Surface finish The standard specimens are smooth, with a Ra better than 0.01 micron. Alternative rougher specimens are available with Ra's of 0.15 or 0.3 micron. Available coatings include pure DLC and Cr doped DLC.

This test reproduces the features of Elastohydrodynamic Lubrication that exists in roller bearing and gear contacts. While there is no related ASTM method the test is well referenced in the open literature. Two types of MTM tests have been performed. The first examines the performance of the lubricant/basestock under constant average speed as the relative sliding of the MTM components is increased. The second method, namely the Stribeck method, examines the effect of changing the average speed. In the latter case, it is possible to measure the friction performance of the test fluids under thin film conditions that exist when the speed is very low.

Low traction as demonstrated in the traction coefficient vs. slide to roll ratio (SRR) is linked to reduced losses in gears and rolling element bearings under EHL conditions. Low friction as demonstrated in the low speed end of the Stribeck curves can be related to improved efficiency in situations where significant interactions between sliding surfaces is expected.

FIGS. 1a-3b show the two types of MTM tests at 0.92 GPa contact pressure in three temperature settings, 40° C., 80° C., 120° C. Relative performance of the fluids at various temperatures is observed. Selected fluids include 5 highly branched functionalized silicone backbone lubricant, 16436-16440, which contain free esters. Selected fluids also include 3 highly branched functionalized silicone backbone lubricant with <=2 wt % free esters, 16614, 16615, 16852. Selected fluids also includes Silicone, 16441, 16442, Ester (C8/C10 TMP Ester), 16443, PAO (40 cSt), 16444, and a water soluble VG 330W PAG as reference.

FIGS. 1a, 2a, and 3a show the relative traction coefficient performance with increased temperature.

At 40° C., all highly branched functionalized silicone backbone lubricants perform better than Silicones and PAO. Sample 16614 is better than the Ester and comparable to the water soluble VG 330W PAG reference.

At 80° C., the performance separation becomes more prominent. The improved performance of all highly branched functionalized silicone backbone lubricants becomes closer, and is significantly better than Silicones, PAO, and TMP Ester.

At 120° C., the same trend continues. The performance of all highly branched functionalized silicone backbone lubricants continue to improve with increased temperature, further separate themselves from Silicones, PAO, and TMP Ester fluids with lower traction coefficient, and become more comparable to the water soluble VG 330W PAG reference.

With this trend, the highly branched functionalized silicone backbone lubricants can be expected to out perform the water soluble VG 330W PAG reference at an environment with even higher temperature.

Figure 2B:
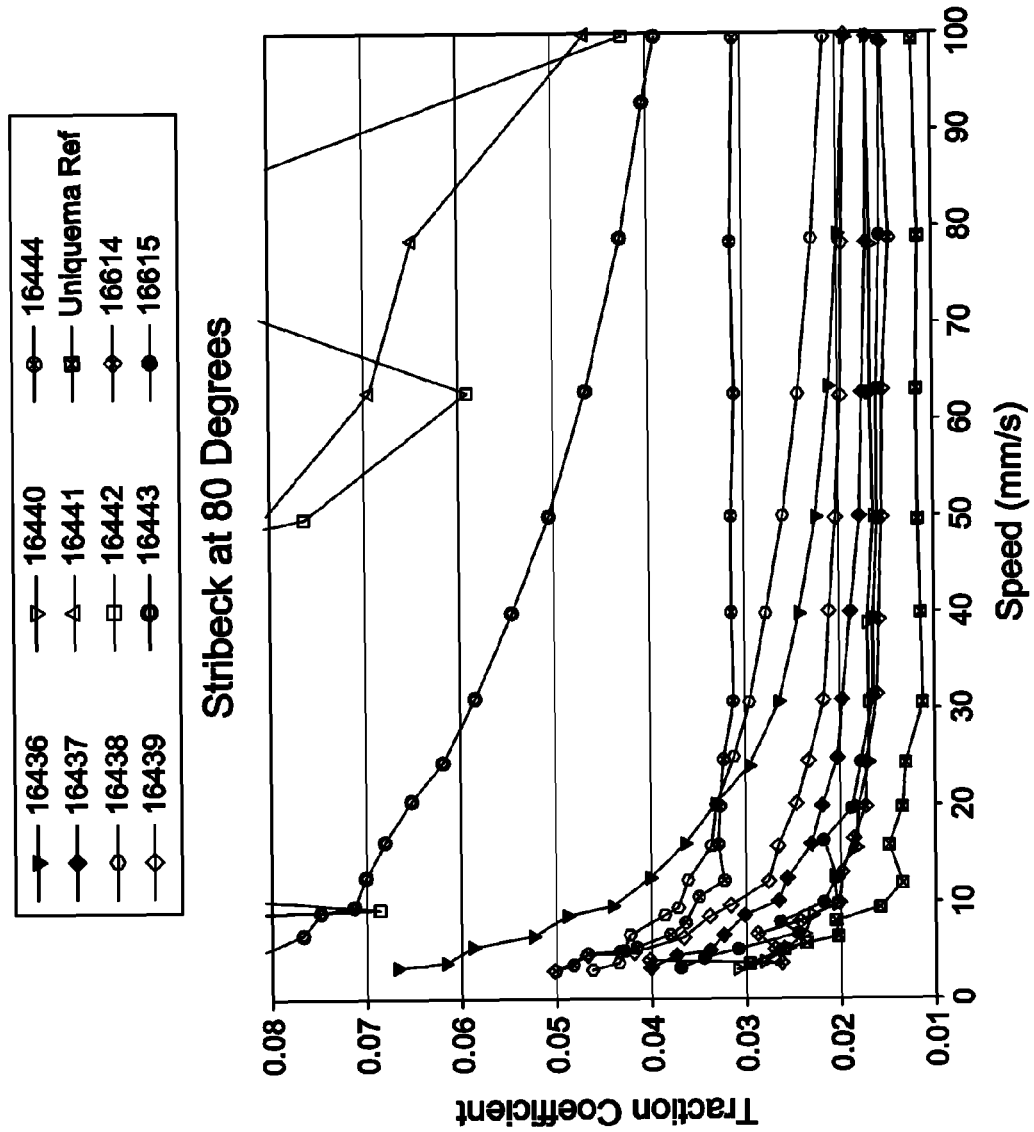
FIG. 2(b) is a chart plotting traction coefficient versus Speed (mm/s) at 80° for various lubricants.

FIGS. 1b, 2b, and 3b show the relative performance of the fluids under thin film conditions at very low speed at the same three temperature settings. As a general observation, the highly branched functionalized silicone backbone lubricants perform better than Silicones, PAO, and TMP Ester, and are comparable to or out perform the water soluble VG 330W PAG reference.

Figure 4A:
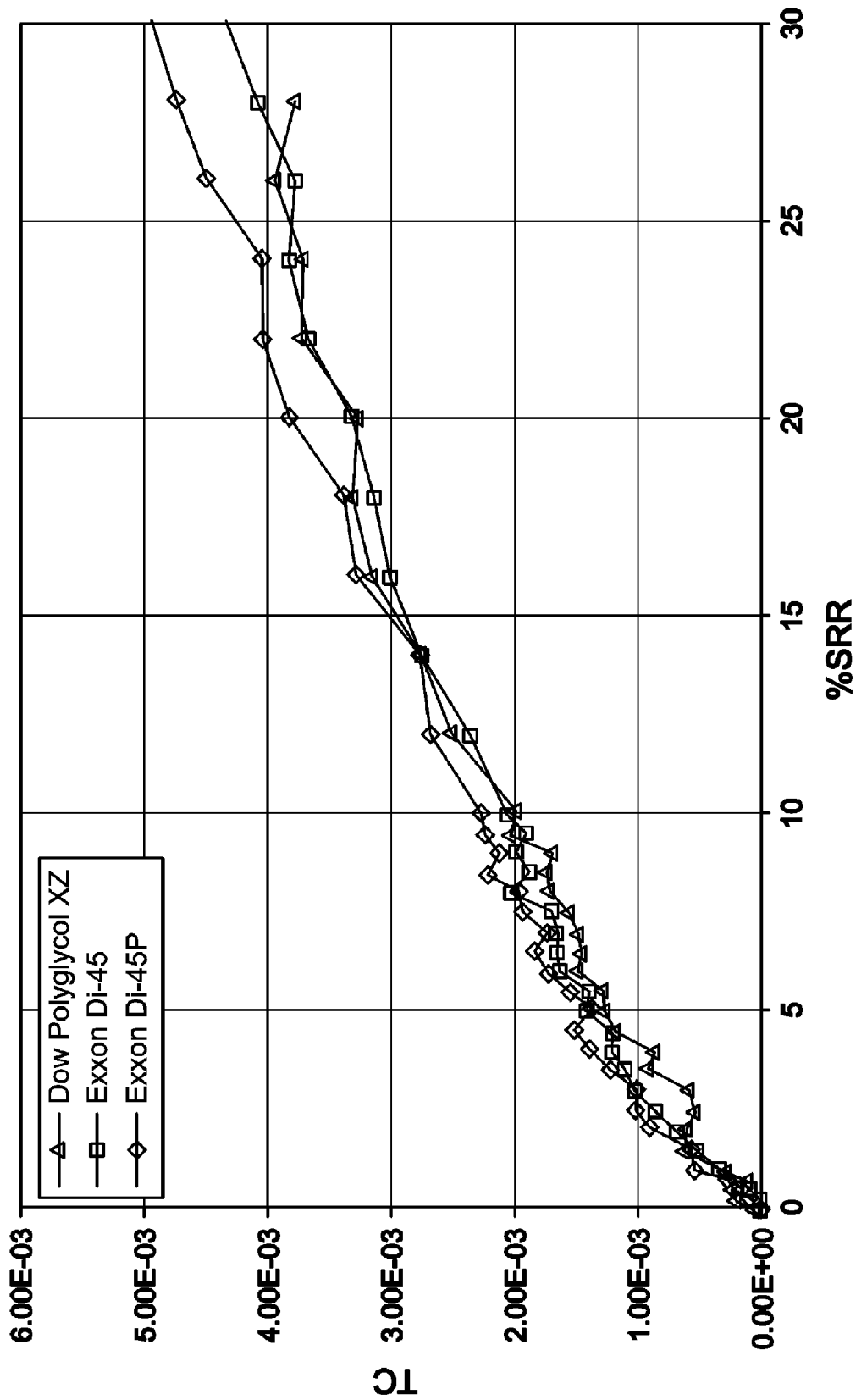
FIG. 4(a) is a chart plotting traction coefficient versus SRR % for Dow Polyglycol XZ, Exxon DI-45 and Exxon DI-45P.

FIG. 4a shows the traction performance of a highly branched functionalized silicone backbone lubricant with residual ester, Exxon Di-45, and without free ester, Exxon Di-45P. They are compared to a commercial PAG at 2 m/s speed, 0.75 GPa pressure setting, and 120° C. temperature. It is apparent that the performance of both highly branched functionalized silicone backbone lubricants are comparable to PAG, and even superior in certain condition required for some specialty lube applications.

To confirm the observation, FIG. 4b shows example of a second highly branched functionalized silicone backbone lubricant with residual ester, Exxon Di-100, with comparable or better performance to commercial PAG at the same test settings.

While the illustrative embodiments of the disclosure have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The disclosure has been described above with reference to numerous embodiments and specific examples. Many variations will suggest themselves to those skilled in this art in light of the above detailed description. All such obvious variations are within the full intended scope of the appended claims.

What is claimed is:

1. A low traction lubricating composition having a traction coefficient of less than or equal to 0.02 as measured using a Mini Traction Machine, said composition comprising a highly branched functionalized silicone backbone composition, wherein said highly branched functionalized silicone backbone composition is a silicone composition having the formula:

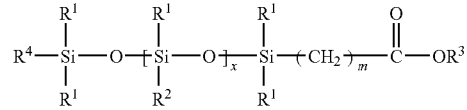

wherein:
$R^1$ are independently selected from the group consisting of: an alkyl having 1-5 carbon atoms, a substituted alkyl having 1-5 carbon atoms optionally substituted by one or more fluorine atoms, and a phenyl, and $R^2$ is selected from the group consisting of: hydrogen, alkyl of 1 to 45 carbon atoms, substituted alkyl of 1 to 45 carbon atoms optionally substituted by one or more fluorine atoms, aryl, a partially esterified ester-containing group represented by the formula:

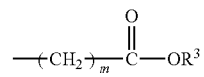

and a reverse ester thereof represented by the formula:

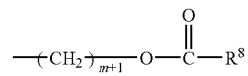

and the formula:

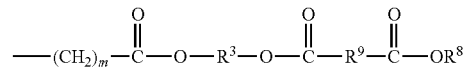

and a reverse ester thereof represented by the formula:

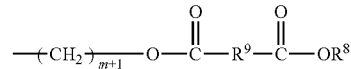

provided that if $R^1$ is anything but methyl or ethyl, then $R^2$ must be a methyl, ethyl or butyl, $R^3$ is derived from a partially esterified ester residue;

$R^8$ is selected from the group consisting of: hydrogen, alkyl of 1 to 45 carbon atoms, substituted alkyl of 1 to 45 carbon atoms optionally substituted by one or more fluorine atoms, aryl and a compound derived from a partially esterified ester residue;

$R^9$ is selected from the group consisting of: an arylene, an alkylene of 1 to 22 carbon atoms, substituted alkylene of 1 to 22 carbon atoms optionally substituted by one or more fluorine atoms and arylene;

$R^4$ is selected from the group consisting of: alkyl of 1 to 45 carbon atoms, substituted alkyl of 1 to 45 carbon atoms optionally substituted by one or more fluorine atoms, aryl, said ester-containing group and said compound derived from reverse esters thereof;

m is an integer between about 5 to about 22; and x is an integer between about 0 to about 1000;

wherein said composition has at least 1 compound derived from said partially esterified ester-containing group or said reverse ester thereof.

2. The composition of claim 1, wherein $R^1$ and $R^2$ are both methyl groups.

3. The composition of claim 1, wherein m is an integer between about 10 to about 14.

4. The composition of claim 1, wherein x is an integer in the range between about 6 to about 110.

5. The composition of claim 1, wherein said compound derived from said partially esterified ester residue is a partially esterified alcohol.

6. The composition of claim 5, wherein said mono-hydroxy-terminated partially esterified alcohol is derived from di-, tri- or tetra-functional alcohol represented by the formula:

wherein:

$R^5$ is an n-functional hydrocarbon; and n is from about 2 to about 8.

7. The composition of claim 6, wherein said functional alcohol is selected from the group consisting of: ethylene glycol, propylene glycol, butylene glycol, polyethylene glycol, neopentyl glycol, polypropylene glycol, glycerin, trimethylolethane, trimethylolpropane, pentaerythritol, di-pentaerythritol, tri-pentaerythritol, and a mixture thereof.

8. The composition of claim 1, wherein said compound derived from said partially esterified ester residue is a partially esterified acid.

9. The composition of claim 8, wherein said mono-hydroxy-terminated partially esterified acid is derived from di-, tri- or tetra-functional acids.

10. The composition of claim 9, wherein said functional acid is selected from the group consisting of: adipic acid, azelaic acid, sebacic acid, dodecanedioc acid, succinic acid, glutaric acid, maleic acid, phthalic acid, trimellitic acid, nadic acid, methyl nadic acid, hexahydrophthalic acid and mixtures thereof.

11. The composition of claim 1, wherein $R^4$ is methyl group.

12. The composition of claim 1, wherein $R^4$ is a group represented by the formula:

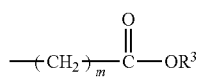

wherein:

$R^3$ is a compound derived from a partially esterified ester residue;

m is an integer in the range between about 5 to about 22; and x is an integer in the range between about 0 to about 1000, or a reverse ester thereof represented by the formula:

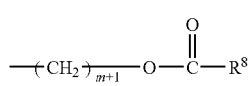

13. The composition of claim 1, represented by the formula:

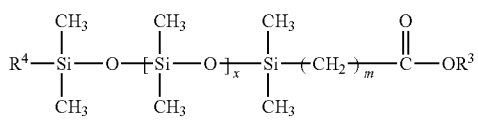

wherein:

$R^4$ is selected from the group consisting of methyl and a group represented by the formula:

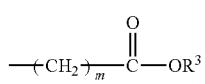

$R^3$ is a compound derived from a partial ester residue;

m is 10; and x is an integer in the range between about 0 to about 1000.

14. The composition of claim 13, wherein $R^4$ is a group represented by the formula:

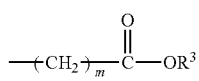

wherein $R^3$ is a compound derived from a partially esterified ester residue.

15. A low traction lubricating composition having a traction coefficient of less than or equal to 0.02 as measured using a Mini Traction Machine, said composition comprising a highly branched functionalized silicone backbone composition, wherein said highly branched functionalized silicone backbone composition is a silicone composition having the formula:

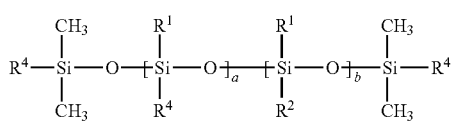

wherein $R^4$ is selected from the group consisting of: alkyl and a group represented by the formula:

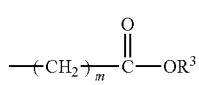

wherein:

a is an integer in the range between about 1 to about 20;

b is an integer in the range between about 0 to about 1000;

$R^3$ is a compound derived from a partially esterified ester residue; and m is an integer in the range between about 5 to about 22;

with the proviso that the $R^4$ groups are not all alkyls.

16. The composition according to claim 1, further comprising at least one other traction reducer fluid.

17. The composition according to claim 16, wherein said other traction reducer fluid is miscible with said highly branched functionalized silicone backbone.

18. The composition of claim 1, further comprising at least one additive selected from the group consisting of: thickeners, VI improvers, pour point depressants, extreme pressure agents, anti-wear additives, friction modifiers, demulsifiers, haze inhibitors, chromophores, anti-oxidants, dispersants, detergents, defoamants, anti-rust additives, metal passivators, limited slip additives, and mixtures thereof.

19. The composition of claim 1, wherein said composition is formulated so as to be suitable for use as an automatic transmission fluid, a manual transmission fluid, an axle lubricant, a transaxle lubricant, an industrial gear lubricant, a circulating lubricant, an open gear lubricant, an enclosed gear lubricant, an hydraulic/tractor fluid, or a grease.

20. The composition of claim 1, wherein said composition is formulated so as to be suitable for use as an automotive gear lubricating composition.

21. The composition of claim 1, wherein said Mini Traction Machine is operated under the following conditions:
   2 m/s entraining velocity,
   a percent slide to roll ratio of 10,
   0.75 inch steel ball loaded against a steel disc, and
   36.58 N applied load and a bulk lubricant temperature of 100° C.

22. The composition of claim 15, wherein said composition is formulated so as to be suitable for use as an automatic transmission fluid, a manual transmission fluid, an axle lubricant, a transaxle lubricant, an industrial gear lubricant, a circulating lubricant, an open gear lubricant, an enclosed gear lubricant, an hydraulic/tractor fluid, or a grease.

* * * * *